United States Patent [19]

Berthold et al.

[11] Patent Number: 5,048,957
[45] Date of Patent: Sep. 17, 1991

[54] SPECIMAN RACK WITH INSERTABLE CUVETTES

[76] Inventors: Fritz Berthold, Euler Weg 9, 7530 Pforzheim; Willy Lohr, Ginsterweg 75, 7547 Wildbad, both of Fed. Rep. of Germany

[21] Appl. No.: 550,494

[22] Filed: Jul. 10, 1990

[30] Foreign Application Priority Data

Jul. 11, 1989 [DE] Fed. Rep. of Germany ....... 3922750

[51] Int. Cl.$^5$ ............................................ G01N 21/03
[52] U.S. Cl. .................................... 356/246; 356/244
[58] Field of Search ....................... 356/246, 434, 244; 436/47; 364/498; 422/64, 67; 211/74

[56] References Cited

U.S. PATENT DOCUMENTS

| | | | |
|---|---|---|---|
| 2,007,087 | 7/1935 | Hird | 356/246 |
| 3,388,807 | 6/1968 | Emmitt | 211/74 |
| 3,551,062 | 12/1970 | Brown | 356/246 |
| 4,305,723 | 12/1981 | Kolber et al. | 356/246 X |
| 4,659,222 | 4/1987 | Ekholm | 356/246 X |
| 4,690,900 | 9/1987 | Kimmo et al. | 356/246 X |

FOREIGN PATENT DOCUMENTS

| | | |
|---|---|---|
| 0148736 | 7/1985 | European Pat. Off. . |
| 0056417 | 10/1986 | European Pat. Off. . |
| 0135502 | 9/1987 | European Pat. Off. . |
| 2451769 | 10/1974 | Fed. Rep. of Germany . |
| 2711853 | 3/1977 | Fed. Rep. of Germany . |
| 3738375 | 12/1987 | Fed. Rep. of Germany . |

*Primary Examiner*—Mark Hellner
*Attorney, Agent, or Firm*—Spensley Horn Jubas & Lubitz

[57] ABSTRACT

A specimen rack composed of a block having a matrix-like arrangement of M×N through chambers, into which M×N cuvettes can be inserted, individually or in the form of strip-racks. Separate connecting strips may be provided to form the strip-racks, and these strips, like the block, are of radiopaque material so that each cuvette, except for a region defined by the lower opening cross section of the through chambers and their upper filling opening, is continuously opaquely shielded from scattering radiation from adjacent cuvettes. Annular shoulders, serving as rests, are dimensioned and disposed in the through chambers such that the vertical position and thus the assay position of the cuvettes in the through chambers can be fixed in defined fashion. Thus the measurement sensitivity on the one hand and possible crosstalk phenomena in the vicinity of the measurement openings on the other can be minimized or optimally adapted to one another.

8 Claims, 3 Drawing Sheets

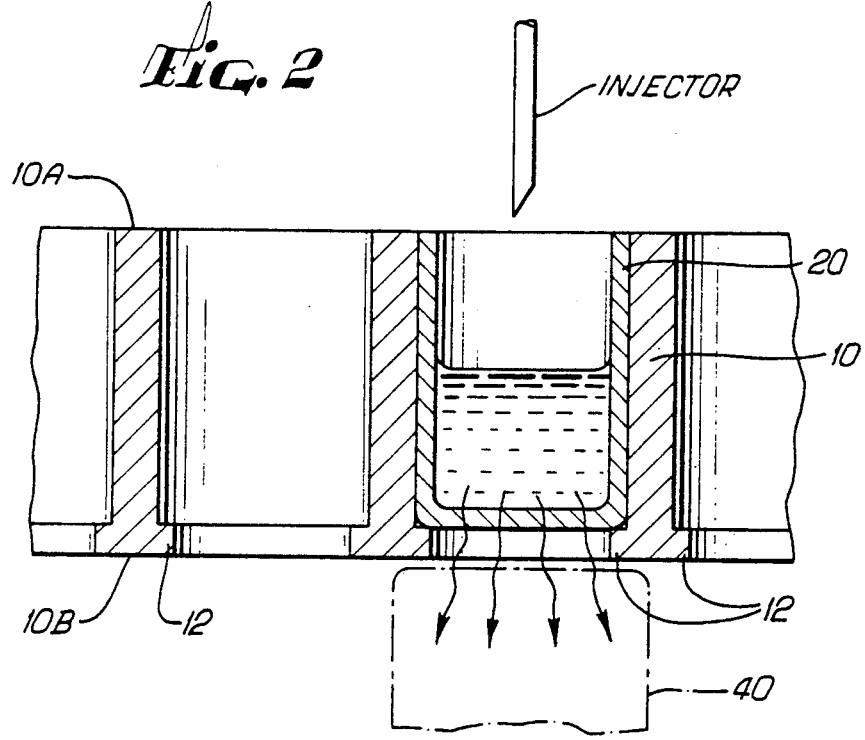
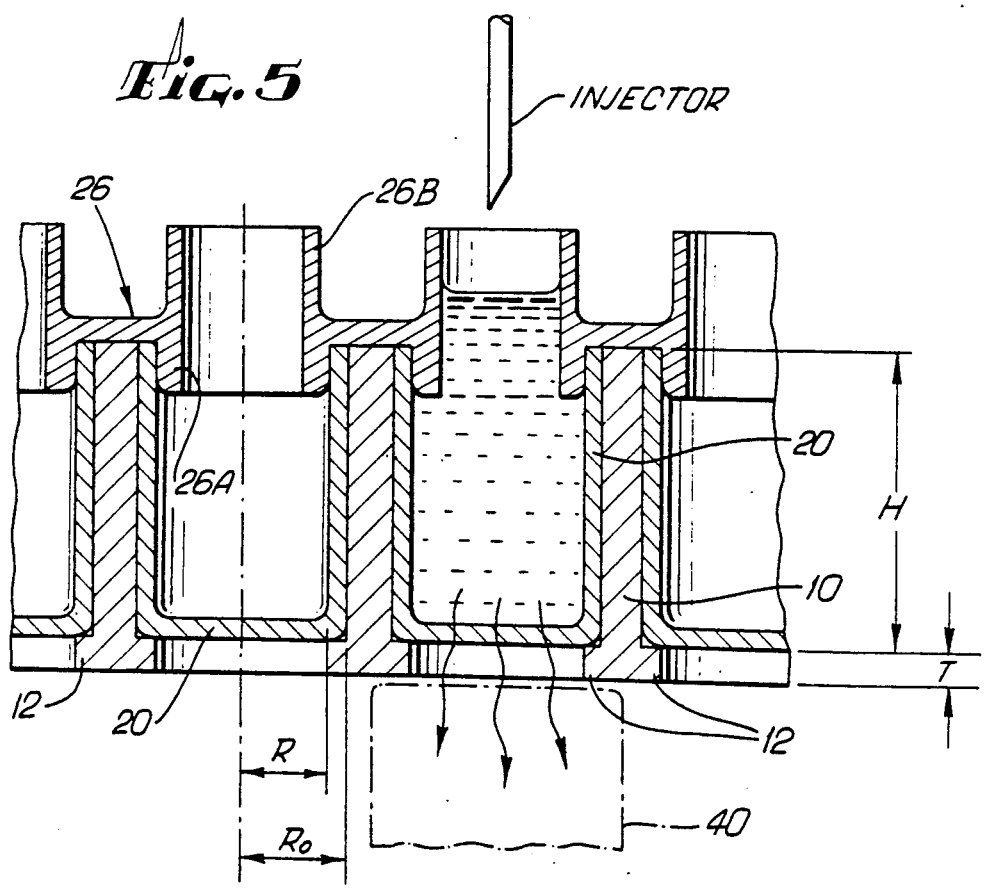

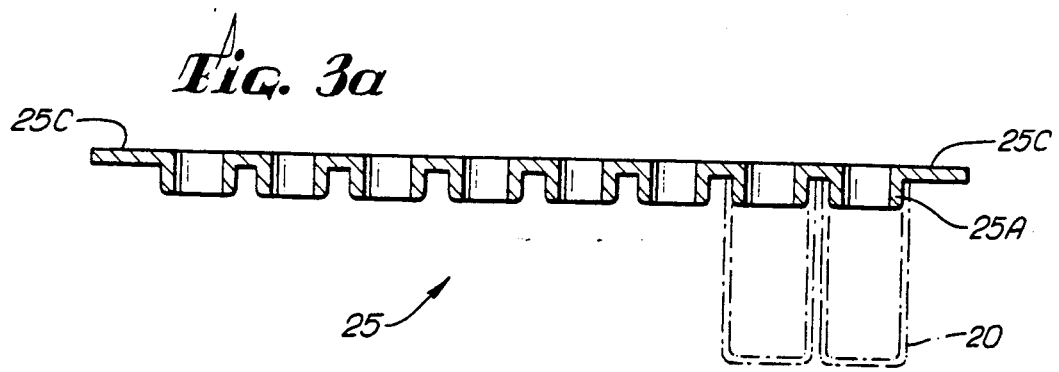
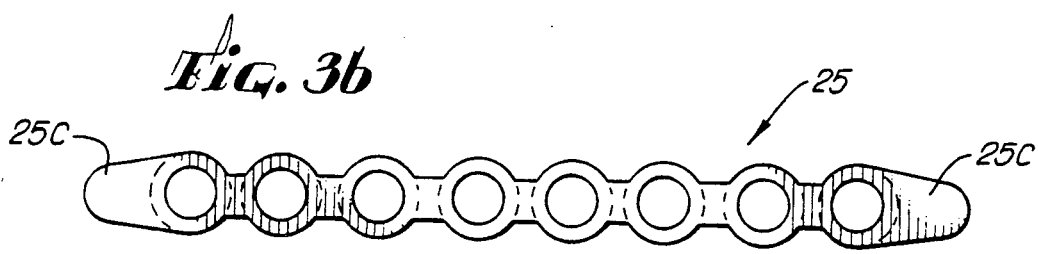
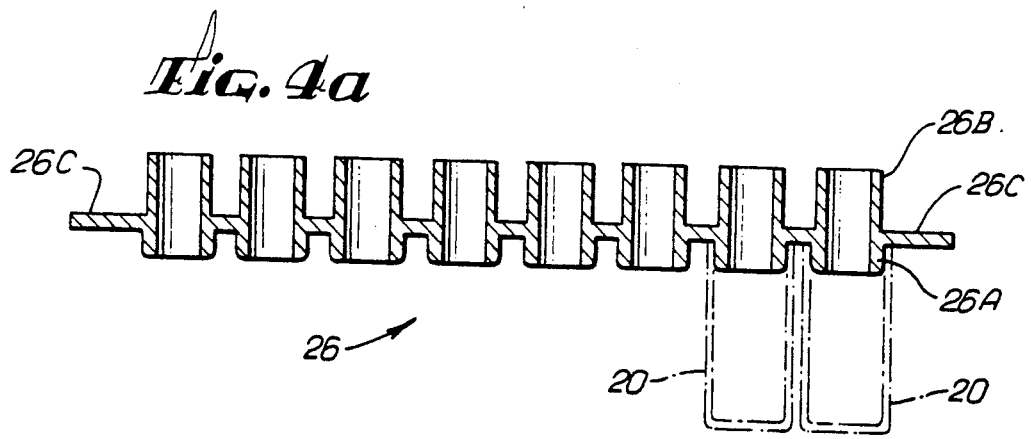
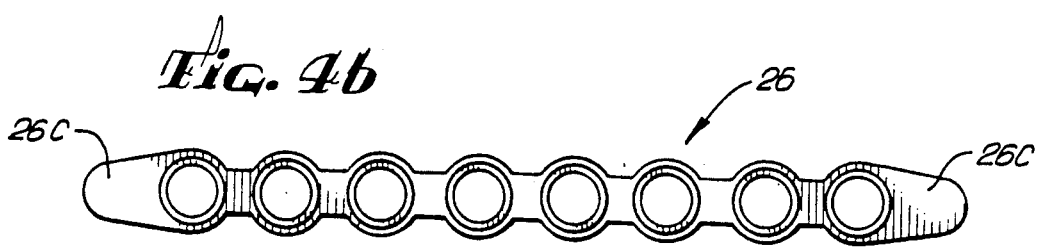

SPECIMAN RACK WITH INSERTABLE CUVETTES

FIELD OF THE INVENTION

The invention relates to a specimen rack with insertable cuvettes, in particular microcuvettes, for performing assays of chemiluminescence or bioluminescence.

BACKGROUND OF THE INVENTION

Specimen racks for receiving cuvettes are widely used in laboratory work. Some such specimen racks are also embodied such that with the cuvettes inserted, they can be passed through or inserted into a number of fixtures and measuring instruments without requiring that the cuvettes be individually removed.

The embodiment of such specimen racks in particular with inserted cuvettes in which the cuvettes remain even during the actual assay naturally depends on the physical nature of the particular assay involved, or in other words on the measuring instrument used on the one hand, and on the character of the radiation to be detected on the other. In specimen racks intended to receive cuvettes on which transmission measurements are intended to be performed, for instance, walls opposite the cuvettes are cut away in order to allow such measurements to be made.

The economy attained with batchwise assays of this kind, on the other hand, involves fundamental problems, however, because of the presence of the "ambient" field of the cuvettes, which is embodied by the material comprising the specimen rack.

On the one hand, the measurement sensitivity is sometimes impaired by the presence of such specimen racks. That is, because the wall thickness of such racks cannot be reduced below a certain minimum, the solid angle engaged by the particular measuring instrument necessarily drops, so that only a fraction of the radiation to be detected can actually be detected; this is particularly disadvantageous in detection processes involving small and/or only brief radiation amplitudes.

On the other hand, the proximity to one another of a plurality of cuvettes allows crosstalk to arise, which falsifies the results of measurement.

If an attempt is made to reduce these effects, for instance by using screens or collimators, that in turn can have negative effects on the measurement sensitivity.

These fundamental problems necessarily increase as the dimensions of the specimen rack and cuvettes decrease; in recent years, for various reasons (for instance to economize on expensive reagents), so called microtitration plates have gained a solid foothold in laboratory technology for performing the applicable radiation measurements; a certain standardization has been attained in terms of the dimensions of these plates, and a relatively large variety of laboratory equipment that fits them, such as automatic washers, is already available on the market. Microtitration plates are usually made in one piece as an injection molded part of plastic, having $8 \times 12 = 96$ specimen wells, or chambers. However, modular assembly of microtitration plates is also possible, by equipping a specimen rack with individual cuvettes or cuvettes assembled into strips, once again resulting in the same grid of $8 \times 12$ specimen positions.

For the reasons explained above, the problems of measurement sensitivity and crosstalk are exacerbated when such microcuvettes or microtitration plates are used, because of the immediate spatial closeness of the various cuvettes or specimen spaces. Therefore, as described in European Patent Document No. 00 56 417, the walls of the holder chambers can be lined with opaque material in order to eliminate the undesirable crosstalk effects, at least in these regions.

In that case, however, given the vertical measurement provided there, the bottom of the microtitration plate must be equipped with an optical window of transparent material, which is expensive for production reasons. The basic problem of crosstalk through such a measurement window is still not eliminated.

This is also true for the filling opening of the microcuvettes or microtitration plate: A great number of important detection methods, particular luminescence immunoassays, require the addition of a suitable reagent, for example by pipette, immediately prior to measurement, in order to induce the reaction to be detected. In practice, this means that an opaque upper covering of the filling openings cannot be provided sufficiently quickly, so that crosstalk from scattered radiation can still arise in this region.

The vulnerability of the various detection methods to the above-described impairments in measurement sensitivity, on the one hand, and to the disturbance caused by crosstalk on the other, depends once again on the nature and on the physical characteristics of the particular detection method, particularly on the intensity and duration of the radiation to be detected, or in other words on its amplitude course over time. For instance, in detection methods in which, because of this amplitude course, the total intensity of radiation to be detected is only slight, care must preferably be taken to attain great measurement sensitivity; but in detection methods offering a correspondingly wide variety of types of radiation, the problem of crosstalk gains greater significance, because even if the measurement of the various microtitration cuvettes is staggered in time, the disturbing radiation of adjacent cuvettes will not yet have faded sufficiently when the next ones are tested.

It has also been proposed in this connection to terminate the chemical reaction actively in one cuvette, before the next cuvette is measured. Such a procedure is disclosed in European Patent No. 0 148 736.

The embodiment of microtitration plates more or less in accordance with European Patent No. 00 56 417 requires a covering hood (limiter 13 in FIGS. 2 and 3 of that patent), which forms partitions between the recessed containers, in order to avoid such crosstalk phenomena.

It is also known to join a plurality of microcuvettes in strips with one another (making what are known as "strip-racks"), in which case, given a mechanically sturdy embodiment of the connecting regions, a microtitration plate that is reduced to a frame can be mounted in place, as described in European Patent No. 0 135 502.

Although this simplifies handling, the above-discussed problems of crosstalk between adjacent cuvettes may be aggravated still further, because the connecting regions may under some circumstances act as optical conductors. For luminescence assays, this design is accordingly unsuitable unless further provisions are made.

SUMMARY OF THE INVENTION

It is therefore an object of the invention to create a structurally simple specimen rack with which both pronounced crosstalk damping and high measurement sensitivity are attainable, particularly for luminescence assays, and which in particular enables the selective use of such strip-racks.

The above and other objects are achieved, according to the invention, by [Insert copy of claim 1]

The holder block can be fabricated relatively simply in one piece, for instance by injection molding, and once the assays have been performed for one set of cuvettes, the block can be reused. The vertical through chambers assure first that the inserted cuvettes, whether they are individual cuvettes or cuvettes joined together as strip-racks, are sealed off from one another in an opaque fashion in their lateral wall regions.

The rests, embodied as annular shoulders, serve to define the assay position of the cuvettes based on the depth to which the cuvettes are inserted into the through chambers. Along with the inside diameter of each annular shoulder, this vertical assay position also, and in particular, determines the solid angle encompassed by the detector (a photomultiplier, for instance), disposed below the through chamber, and thus directly determines not only the crosstalk damping in this range of "coupling" to the detector, but also the measurement sensitivity: The higher the bottom of the cuvette is located relative to the underside of the block in its assay position, and the smaller the inside diameter of the annular shoulder, the smaller is the solid angle that the detector can encompass. Accordingly, the annular shoulder also acts as a diaphragm. Given a constant inside diameter of the annular shoulder, a very low positioning of the cuvette, for instance with the bottom of the cuvette virtually flush with the underside of the block, consequently leads to a large solid angle and thus high measurement sensitivity; a cuvette positioned higher up in the through chamber does decrease the effective solid angle, but increases the crosstalk damping with respect to adjacent through chambers. The inside diameter of the annular shoulder can be varied with corresponding effects. Depending on the type of detection method, as described above, both the height and the inside diameter of the annular shoulders can accordingly be selected such that optimization of both these values (crosstalk damping and measurement sensitivity) is attainable.

According to a particularly advantageous embodiment of the invention, the cuvettes are connected to one another to make a strip rack via a separate connecting strip of radiopaque material, in particular via cylindrical extensions on the connecting strip which protrude into the cuvettes and hold them by frictional engagement.

When radiopaque material such as black polyethylene is used, the filling region of the cuvettes is also protected against crosstalk phenomena.

This variant can be further embodied such that, in addition to the lower cylindrical extensions, the connecting strip has upper cylindrical extensions as well, which are coaxial with the lower ones.

This increases the capacity of the cuvette for the applicable fluid, and this assures that once again the entire wall region of the cuvette is opaque; particularly in the region of the filling opening, crosstalk is reliably prevented by the laterally projecting walls of the upper extensions made of the opaque material. In addition, this upper cylindrical attachment can provide sealing off of the injector.

The invention will now be described in further detail with reference to exemplary embodiments shown in the drawings.

BRIEF DESCRIPTION OF THE DRAWINGS

FIG. 2 is an elevational cross-sectional detail view through the block of FIG. 1, with a single cuvette inserted.

FIG. 3a is an elevational cross-sectional view of a first exemplary embodiment of a connecting strip for combining a plurality of cuvettes into a strip-rack.

FIG. 3b is a bottom plan view of the strip of FIG. 3a.

FIGS. 4a and 4b are views similar to those of FIGS. 3a and 3b of a second exemplary embodiment of a connecting strip.

FIG. 5 is a view similar to that of FIG. 2 through the block of FIG. 1 with cuvettes inserted and joined together via the connecting strip of FIGS. 4.

DESCRIPTION OF THE PREFERRED EMBODIMENTS

Figure 1:
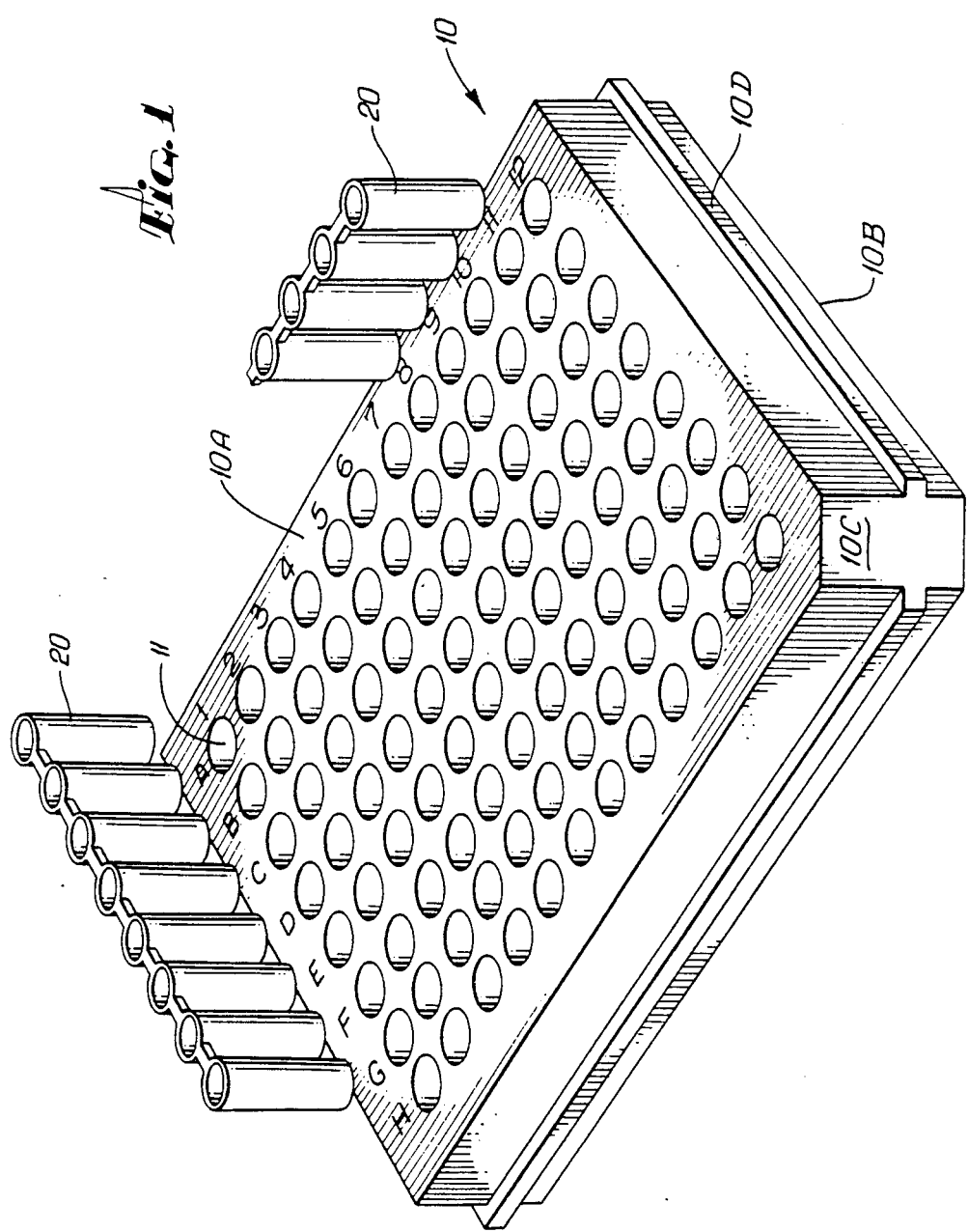
FIG. 1 is a perspective view of a block for holding cuvettes according to the invention.

The specimen rack shown in FIG. 1 is composed of a flat, substantially cuboid block 10 of radiopaque, solid, dimensionally stable and deformation-resistant material, such as aluminum, which may be anodized black in order to reduce light reflections.

A number of through bores, or through chambers, 11 are formed in a matrix-like pattern and extend completely from the top 10A to the bottom 10B of block 10. The rows of bores 11 are identified by capital letters, and the columns are identified by numbers In the exemplary embodiment shown, 8×12=96 such through bores 11 are provided. These through bores 11 may then either hold single cuvettes, or so-called strip-racks, as schematically shown in FIG. 1, preferably strip-racks of the kind in which either 8 or 12 cuvettes 20 are joined together in strips by means of connecting strips at the filling openings of the cuvettes, so that each strip-rack occupies a full row or column of the block 10.

To make the cuboid block 10 non-symmetrical, it is provided with a slanted, or. chamfered, side surface 10C. This shape helps to avoid positioning errors when various measurement steps are performed.

The block 10 is also equipped with a surrounding bead 10D in order to assure an accurate local position in the holder plate of a measuring instrument in the X-Y-Z axes.

In the embodiment of block 10 shown in FIGS. 2 and 5, the through chambers 11 have a reduced cross section at their lower end oriented toward a detector 40, thus forming an annular shoulder 12 there that defines the exit cross section of the radiation to be measured and also defines the vertical measuring position of a flat-bottomed, cuvette 20 when the cuvette rests with its bottom edge on the annular shoulder 12; the radius R of the opening defined by annular shoulder 12 and the thickness T of annular shoulder 12 thus define the solid angle of radiation to be detected that can be encompassed by the detector 40.

If one wishes to use strip-racks instead of individual cuvettes, then FIGS. 3 and 4 show two exemplary embodiments of connecting strips 25 and 26, respectively, which like block 10, are made from material opaque to light, and the lower cylindrical extensions 25A and 26A of which engage the open upper ends of cuvettes 20 in the manner of plugs and thus position cuvettes 20 with respect to one another, because the underside of the connecting regions between these cylindrical extensions 25A, 25B form stops for the upper edges of cuvettes 20.

In the second exemplary embodiment of a connecting strip 26 of this kind, shown in FIG. 4, in addition to lower cylindrical extensions 26A that serve to hold cuvettes 20, there are other cylindrical extensions 26B integrally formed at the top, which increase the usable volume of the cuvette; this may be useful in some detection methods to increase the radiation yield, or to prevent fluid from splashing out when reagents are injected.

A common feature of both variants of FIGS. 3 and 4 is that because of the radiopacity of the material used for the connecting strips 25, 26, the filling region of each cuvettes is likewise shielded in a photoopaque manner from adjacent cuvettes.

To make it easier to press such connecting strips onto, and remove them from, the proper number of cuvettes, extensions 25C, 26C are formed onto both ends of the connecting strips to serve as handling tabs.

The connecting strips 25, 26 can each be preferably made in one piece, for instance as injection molded parts.

FIG. 5, in a cross-sectional view corresponding to FIG. 2, shows the disposition of a plurality of cuvettes 20 in the block 10, with cuvettes 20 being coupled to one another via a connecting strip 26. The "seamless" transition from the opaque material of block 10 to connecting strip 26 can be seen, which prevents photoconduction effects between adjacent cuvettes.

For a practical luminescence assay, the following dimensions are selected for the through chambers/cuvettes:

Radius $R_o$ of the through chambers 11: 4 mm
Inside radius R of the annular shoulder 12: 3.25 mm
Thickness T of the annular shoulder 12: 0.5 mm
Height H of cuvettes 20 used: 14 mm This application relates to subject matter disclosed in Federal Republic of Germany Application No. P 39 22 750.2, filed on July 11, 1989, the disclosure of which is incorporated herein by reference.

While the description above refers to particular embodiments of the present invention, it will be understood that many modifications may be made without departing from the spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

We claim:

1. A specimen rack for holding a plurality of insertable cuvettes for performance of bioluminescence and chemiluminescence assays, comprising a holder block of radiopaque and dimensionally stable material, said block having opposed upper and lower major surfaces and being provided with a plurality of through chambers extending between said upper and lower major surfaces and arranged in a rectangular array composed of a plurality of rows and columns of through chambers for receiving and positioning a corresponding plurality of the cuvettes, so that when the cuvettes are inserted in said chambers, the material of said block forms an opaque enclosure for the inserted cuvettes over at least a portion of the height of the cuvettes, wherein said block is formed such that each said through chamber has an inner wall and an annular shoulder extending radially inwardly from said inner wall to define a rest for supporting a respective cuvette, the annular shoulder determining the insertion depth and thus the assay position of the respective cuvette in said through chamber.

2. The specimen rack of claim 1 in combination with means defining a strip-rack for holding a number of cuvettes equal to the number of rows or columns of the rectangular array of through bores.

3. The specimen rack of claim 2 wherein said means defining a strip-rack comprises a connecting strip of radiopaque material for holding the cuvettes.

4. The specimen rack of claim 3 wherein said connecting strip has a plurality of lower cylindrical extensions each dimensioned to extend into, and frictionally engage, a respective cuvette.

5. The specimen rack of claim 4 wherein said connecting strip additionally has upper cylindrical extensions which are located coaxially with said lower extensions.

6. The specimen rack of claim 3 wherein said connecting strip has two opposed ends provided with handling tabs.

7. The specimen rack of claim 6 wherein said connecting strip is formed in one piece from black polyethylene.

8. The specimen rack of claim 3 wherein said connecting strip is formed in one piece from black polyethylene.

* * * * *